(12) United States Patent
Nacson et al.

(10) Patent No.: US 7,458,283 B2
(45) Date of Patent: Dec. 2, 2008

(54) ARTICLE SCANNER

(75) Inventors: Sabatino Nacson, Thornhill (CA); Duncan Gibbons, Whitby (CA)

(73) Assignee: Smiths Detection Inc., Ontario (CA)

( * ) Notice: Subject to any disclaimer, the term of this patent is extended or adjusted under 35 U.S.C. 154(b) by 314 days.

(21) Appl. No.: 11/319,201

(22) Filed: Dec. 28, 2005

(65) Prior Publication Data
US 2008/0264186 A1   Oct. 30, 2008

Related U.S. Application Data

(60) Provisional application No. 60/640,090, filed on Dec. 30, 2004.

(51) Int. Cl.
*G01N 1/22* (2006.01)
(52) U.S. Cl. ................................... 73/863.12
(58) Field of Classification Search ............... 73/863.12
See application file for complete search history.

(56) References Cited

U.S. PATENT DOCUMENTS

| | | | |
|---|---|---|---|
| 5,071,771 A | | 12/1991 | Barbour et al. |
| 5,109,691 A | * | 5/1992 | Corrigan et al. ............ 73/23.36 |
| 5,405,781 A | | 4/1995 | Davies et al. |
| 5,476,794 A | * | 12/1995 | O'Brien et al. ............... 436/92 |
| 5,571,976 A | * | 11/1996 | Drolet ..................... 73/864.71 |
| 5,741,984 A | * | 4/1998 | Danylewych-May et al. ....................... 73/864.71 |
| 5,859,375 A | * | 1/1999 | Danylewych-May et al. ....................... 73/864.71 |
| 6,446,514 B1 | * | 9/2002 | Danylewych-May et al. ....................... 73/863.21 |
| 6,613,571 B2 | * | 9/2003 | Cordery et al. ............... 436/48 |
| 2004/0016310 A1 | * | 1/2004 | Sakairi et al. ................. 73/866 |

FOREIGN PATENT DOCUMENTS

| | | |
|---|---|---|
| CA | 2190070 | 5/1998 |
| EP | 0 447 158 A2 | 9/1991 |

\* cited by examiner

*Primary Examiner*—Robert R Raevis
(74) *Attorney, Agent, or Firm*—Foley & Lardner LLP

(57) ABSTRACT

A CTD and method of using a CTD for automatic sampling and analysis of target analytes, such as explosive materials, chemical warfare agents, and narcotics present on documents or other articles is provided. The CTD comprises an article processing mechanism, a swabbing medium, a thermal desorber, and a spectrometer.

34 Claims, 9 Drawing Sheets

ARTICLE SCANNER

BACKGROUND

Screening for explosive materials and illegal narcotics is now routine in airports, train stations, sports arenas, and other industries charged with handling large volumes of individuals, individuals and their belongings must be screened for explosive materials and explosive residues. While it is desirable to identify individuals carrying illegal narcotics, it is particularly important from a security standpoint, to screen individuals for the presence of explosive materials. Trace amounts of explosive materials remain on the skin of an individual who has handled them, because trace explosive materials are difficult to remove. Thus, trace amounts of explosive materials are transferred to articles and documents handled by an individual with explosive-contaminated hands. For example, investigation of particle transfer mechanisms from contaminated hands to documents using the explosive materials Semtex, TNT and nitroglycerin show that traces of these compounds can be detected on hands up to 48 hours after handling the materials. Consequently, screening and individual's articles and documents for trace amounts of explosive materials provides a reliable means for detecting explosive materials present on an individual or in their belongings. Because not every individual will have luggage or other article with them, screening an article, such as a travel ticket, boarding pass, passport or other identification card, or credit card is a non-invasive means of testing the individual's hands for the presence of explosive materials illegal narcotics.

Several methods have been used to for the screening of documents. One method involves manually rubbing each individual article with a swab (referred to as the "dry transfer technique"), placing the swab into an ion mobility spectrometer (IMS) sample holder, heating the sample to thermally desorb the sample, and analyzing the sample by IMS. Although it has been established that this method is optimal for trace detection of explosive materials present on an article or article, this method is cumbersome, time-consuming, and potentially inconsistent because each article must be handled individually the sample collection step is subject to human error, such as failure to apply sufficient pressure when obtaining a sample.

Another technique employs infrared heating of an article to vaporize a sample to be analyzed. This method suffers significant drawbacks. First, the indiscriminate nature of the infrared vaporization releases a complex mixture of compounds from an article, including natural oils on fingers, ink components, binders and fillers used in the manufacture of the ticket or article stock. Because the vaporization can yield a very complex sample, detection and analysis of the sample require a tandem mass spectrometer (MS-MS) to qualify the species present. Second, the paper stock used for tickets and other documents can be heat-sensitive, making the end product very susceptible to physical and chemical degradation as a result of direct heating.

For example, a direct heating method, using infrared to heat an article, e.g. a boarding pass, was developed by MSA/Sciex. A stream of air flowed through the article and passed into the ionization region of an MS-MS carries vaporized components from the pass to the ionization region. In order to vaporize non-volatile explosive materials, such as RDX, TNT and PETN, the temperature of the heating source is increased to 150-180° C. At these temperatures damage to the article can occur, including damage to a ticket having a magnetic strip.

Thus, there is a need in the art for a simple, rapid means for screening documents for trace analytes.

SUMMARY

Accordingly, a contact trace detector apparatus is provide which rapidly and automatically collects a sample from an article and analyzes the sample for the presence of trace amount of target analytes.

According to one embodiment, a contact trace detector is provided. The contact trace detector comprises an article processing mechanism for moving an article through the detector, a swabbing medium for collecting an analyte from the article, a thermal desorber, and a spectrometer with an inlet for receiving the analyte.

According to another embodiment, a method of testing an article is provided. The method comprises inserting an article into a detector, the article having a first surface and a second surface, contacting a first surface of the article with a first swabbing medium, transferring an analyte to the swabbing medium, and analyzing the analyte.

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages will become apparent from the following description, appended claims, and the accompanying exemplary embodiments shown in the drawings, which are briefly described below.

DETAILED DESCRIPTION

Figure 5:
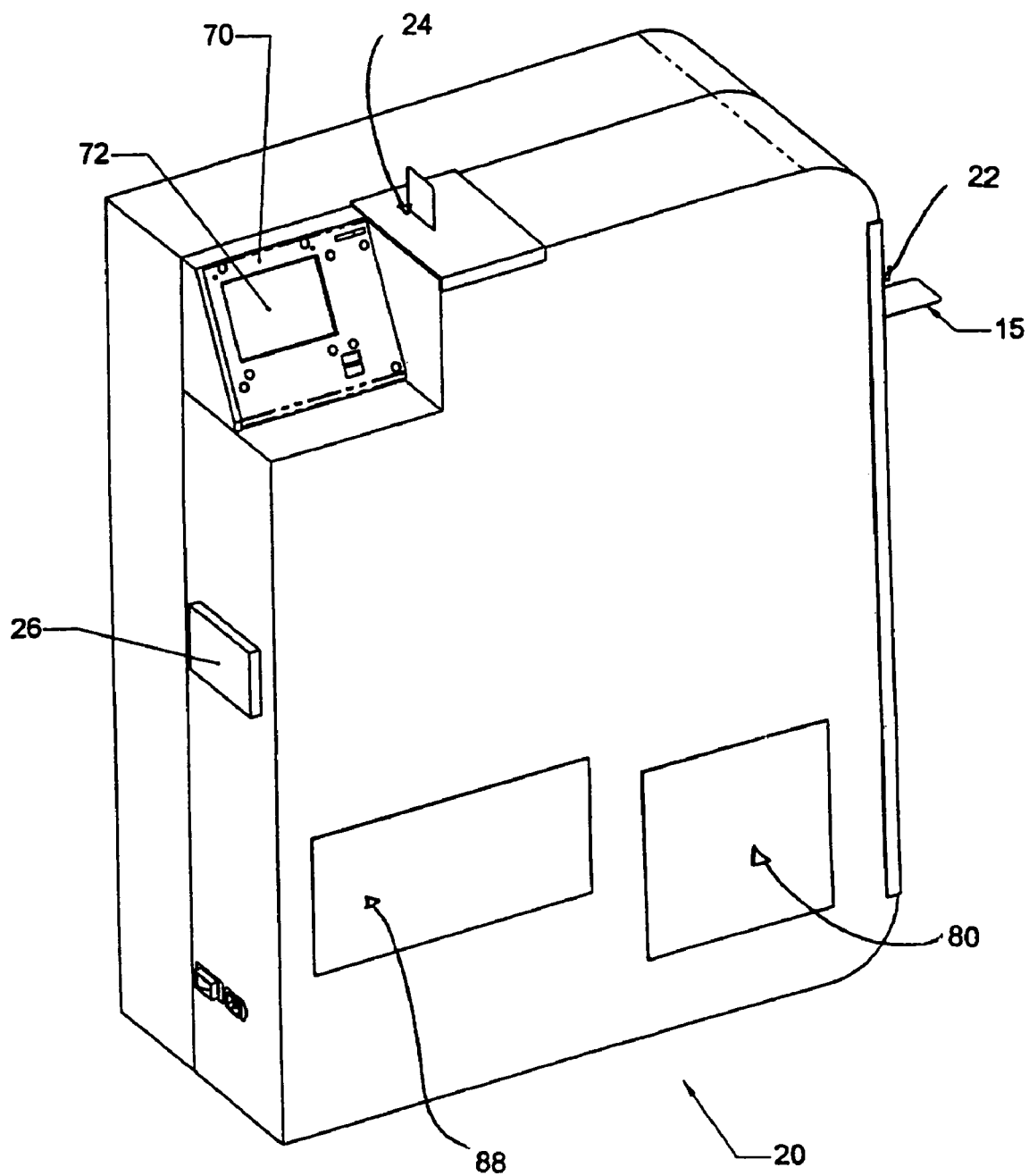
FIG. 5 is a perspective view of the contact trace detector according to FIG. 1.

An apparatus, referred to as a contact trace detector 20 (CTD) for the detection of trace target analyte present on articles or documents 15 to be tested is provided. The CTD 20 shown in, for example, FIGS. 1 and 5, includes an article processing mechanism 30, swabbing medium 40, a thermal desorber 50, and a spectrometer 60.

"Approximately" and "substantially," as it is used herein, generally refers to a variation of less than 10% to less than 20% from a given value and is meant to allow for error inherent in measurement techniques as well as differences in measurement values obtained when measurements are performed using different techniques. "Sample" refers, without limitation, to any molecule, compound or complex that is adsorbed, absorbed, or imbedded in the structure of a swabbing medium 40.

The CTD 20 is useful for analyzing a wide range of analytes, including but not limited to explosive materials, narcotics, chemical warfare agents, toxins and other chemical compounds. A sample can contain an analyte of interest, referred to herein as an "analyte," "target analyte," or "sample analyte," which is understood to be, without limitation, any molecule, compound or complex, the presence of which is to be detected using a detection technique. Target analytes include, without limitation, explosive materials, chemical warfare agents, and narcotics.

Explosive materials which can collected and analyzed by the CTD 20 include, but are not limited to, 2-amino-4,6-dinitrotoluene, 4-amino-2,6-dinitrotoluene, ammonal, ammonium nitrate, black powder, 2,4-dimethyl-1,3-dinitrobutane, 2,4-dinitrotoluene, ethylene glycol dinitrate, forcite 40, GOMA-2, hexanitrostilbene, 1,3,5,7-tetranitro-1,3,5,7-tetrazacyclooctane (HMX), mononitrotoluene, nitroglycerine, pentaerythritol tetranitrate (PETN), 1,3,5-trinitro-1,3,5-triazacyclohexane (RDX), semtex-A, Semtex-H, smokeless powder, trinitro-2,4,6-phenylmethylnitramine tetryl (Tetryl), 2,4,6-trinitrotoluene (TNT), trilita, and 1,3,5-trinitrobenzene and combinations of these compounds. In one embodiment, the explosive which are collected are 1,3,5-trinitro-1,3,5-triazacyclohexane, pentaerythritol tetranitrate, 2,4,6-trinitrotoluene, trinitro-2,4,6-phenylmethylnitramine tetryl, nitroglycerine, ammonium nitrate, 3,5,7-tetranitro-1,3,5,7-tetrazacyclooctane, and combinations thereof.

Narcotics which can be collected and analyzed, include but are not limited to 6-acetylmorphine, alprazolam, amobarbital, amphetamine, antipyrine, benzocaine, benzoylecgonine, bromazepam, butalbital, carbetapentane, cathinone, chloradiazepoxide, chlorpheniramine, cocaethylene, cocaine, codeine, diazepam, ecgonine, ecognine methyl ester (EME), ephedrine, fentanyl, flunitrazepam, hashish, heroin, hydrocodone, hydromorphone, ketamine, lidocaine, lorazepam, lysergic acid diethylamide (LSD), lysergic acid, N-methyl-1-3(3,4-methylenedioxyohenyl)-2-butanamine (MBDB), 3,4-methylenedioxyamphetamine (MDA), DL-3,4-methylenedioxyethylamphetamine (MDEA), methylenedioxymethamphetamine (MDMA), marijuana, mescaline, methadone, methamphetamine, methaqualone, methcathinone, morphine, noscapine, opium, oxazepam, oxycodone, phencyclidine (PCP), pentobarbital, phenobarbital, procaine, psilocybin, secobarbital, temazepam, THC, THC—COOH, and triazolam. In one embodiment, the narcotics which can be collected with a swabbing medium 40 include cocaine, heroin, phencyclidine, THC, methamphetamine, methylenedioxyethylamphetamine, methylenedioxymethamphetamine, N-methyl-1-3(3,4-methylenedioxyohenyl)-2-butanamine, lysergic acid diethylamide, and combinations thereof.

Chemical warfare agents and other toxins that can be collected and analyzed include, but are not limited to amiton (VG), anthrax, arsine, cyanogen chloride, hydrogen chloride, chlorine, diphosgene, PFIB, phosgene, phosgene oxime, chloropicrin, ethyl N,N-dimethyl phosphoramicocyanidate (Tabun), isopropyl methyl phosphonofluoridate (Sarin), pinacolyl methyl phosphonefluoridate (Soman), phosphonofluoridic acid, ethyl-, isopropyl ester (GE), phosphonothioic acid, ethyl-, S-(2-(diethylamino)ethyl) O-ethyl ester (VE), phosphonothioic acid, methyl-, S-(2-(diethylamino)ethyl) O-ethyl ester (VM), distilled mustard, ethyldichloroarsine, lewisite 1, lewisite 2, lewisite 3, methyldichloroarsine, mustard-lewisite mixture, mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-(bis(1-methylethyl)amino)ethyl) O-ethyl ester (VX), cyclohexyl methylphosphonofluoridate (GF), and combinations thereof.

The CTD collects a sample from an article to be analyzed to determine the presence of a target analyte. The CTD article processing mechanism 30 moves an article 15 from a front opening or entrance 22, through the CTD 20 and out to an exit 24. The article 15 can be any type of suitable article or document 15. In one embodiment, the article 15 is a travel ticket, boarding pass, passport, identification card, driver's license, or credit card.

Figure 4:
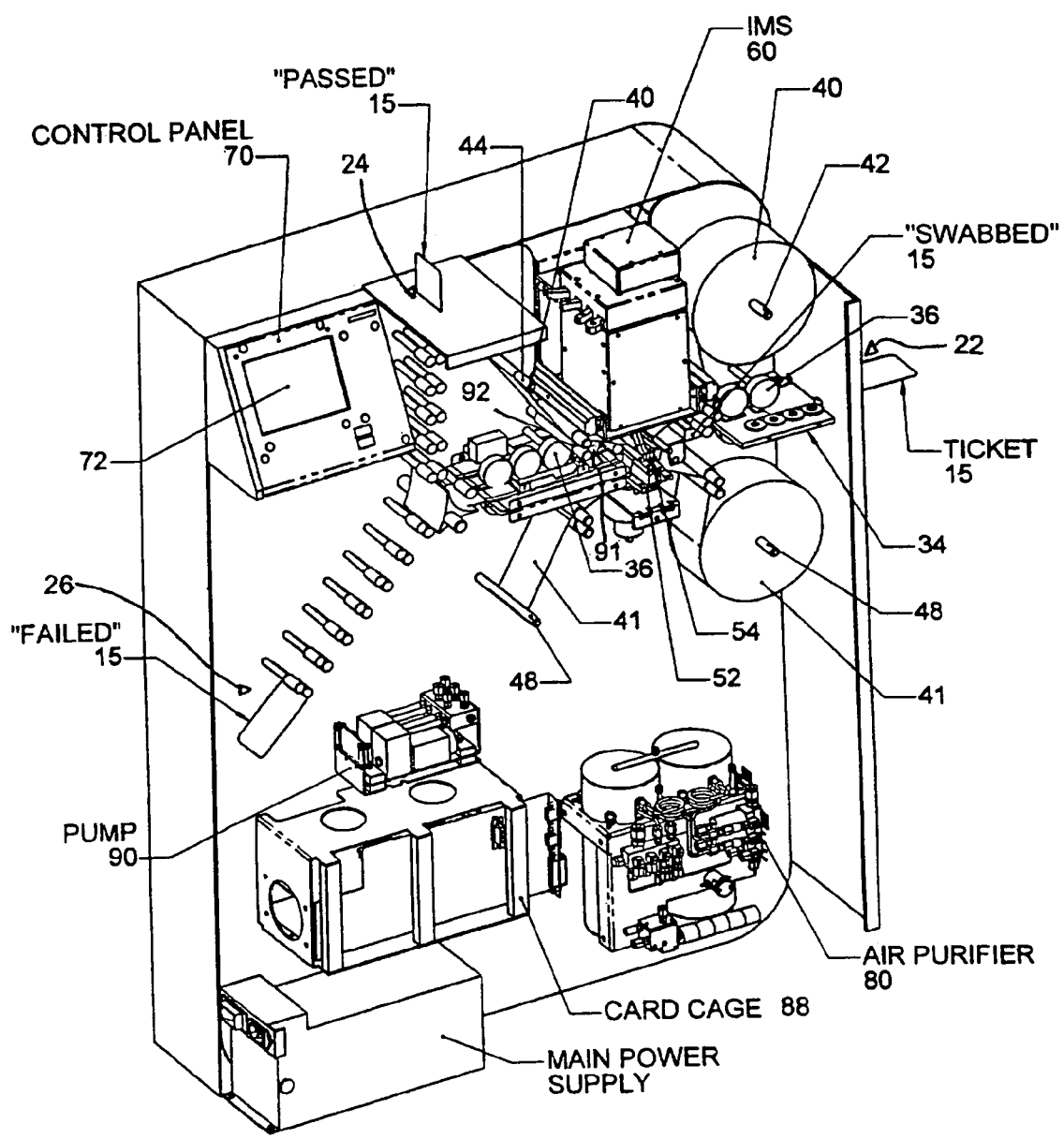
FIG. 4 is an extruded view of the contact trace detector according to FIG. 1.

An article processing mechanism 30, according to an embodiment shown in FIGS. 1-3 and 7, comprises at least one roller 32, which guides an article 15, positioning the article 15 adjacent to a swabbing medium 40 and into a holding area or out to the exit 24. The article 15 is moved through the CTD 20 by a series of rollers 32 and a guide bed 34. The rollers 32 may be positioned adjacent to, above, or on the guide bed 34. The article 15 is positioned on the guide bed 34 between the rollers 32, after being inserted through an entrance 22, and moved in the forward and/or reverse direction by the guide bed 34 and the rollers 32. The article 15 weaves and/or slides between the rollers 32, moving the article in a forward and reverse direction adjacent to the swabbing medium 40 and the spectrometer 60, and forward along a first path leading to an exit 24 or along a second path direct to a holding area 26, as shown in FIG. 4. The rollers 32, in one embodiment, can apply a substantially constant tension against the article 15, to keep the article 15 in position. The rollers 32 are be driven by electrical motors, which drive one or more pulleys, belts, gears, or any other suitable mechanism.

The article processing mechanism 30 includes a switch mechanism 91 to change the path of the article 15 from a first path directed to exit 24 to a second path directed to a holding area 26, as seen in FIG. 4. The switch mechanism 91 includes at least one switch roller 92, which alternates between two travel paths, directing the article 15 to either a first path to an exit 24 or to a second path directed the holding area 26. The triggering mechanism for diverting the article 15 is keyed to a detection system (discussed below), which detects the presence of a target analyte. If the detection system identifies a target compound, an alarm is obtained, a signal is sent to activate a solenoid (not shown), which causes a switch mechanism 91 to engage the switch roller 92 and divert the article 15 to a "non-passed" or holding area 26 direction.

Figure 8:
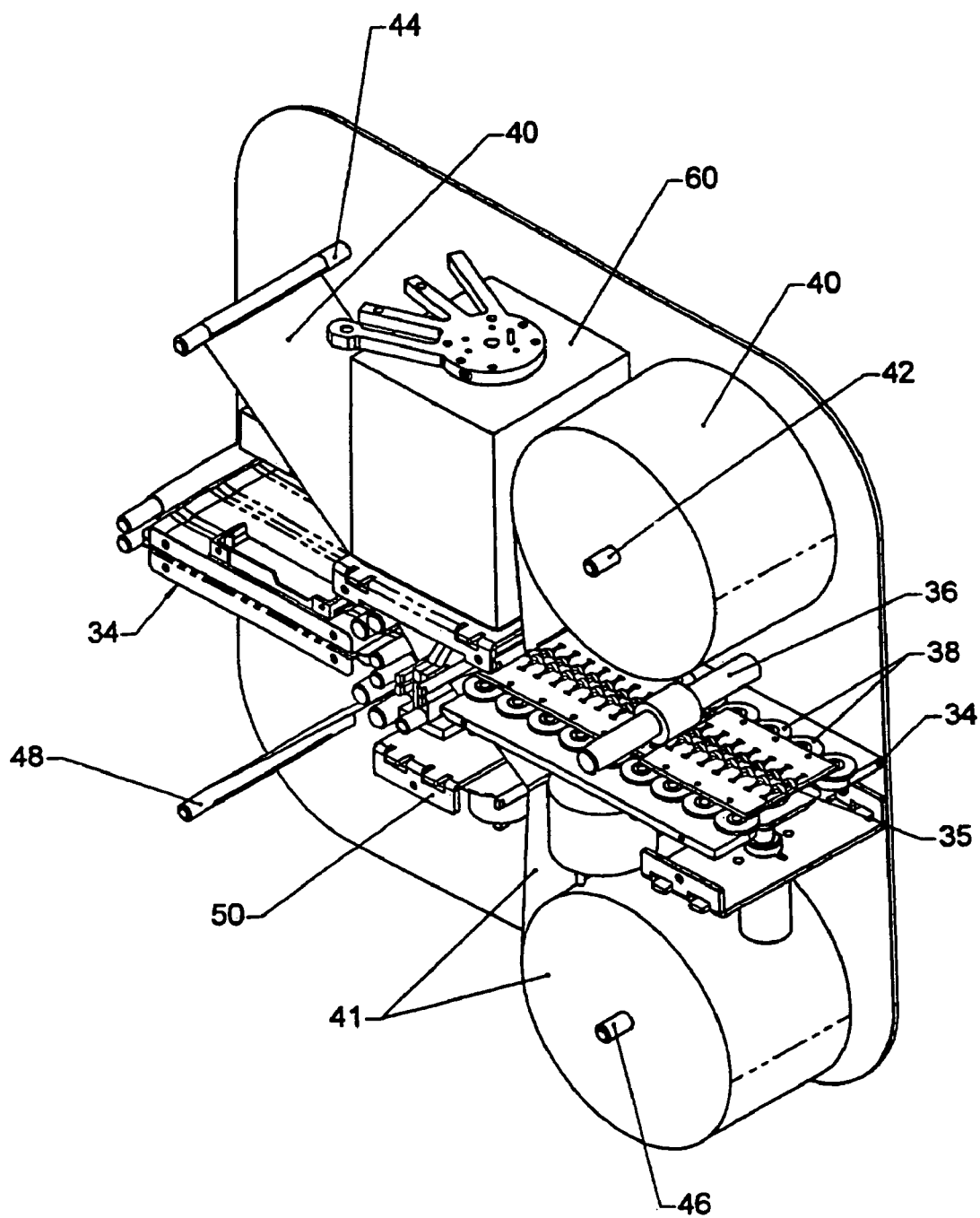
FIG. 8 is a perspective view of a contact trace detector according to another embodiment of the invention.
Figure 9:
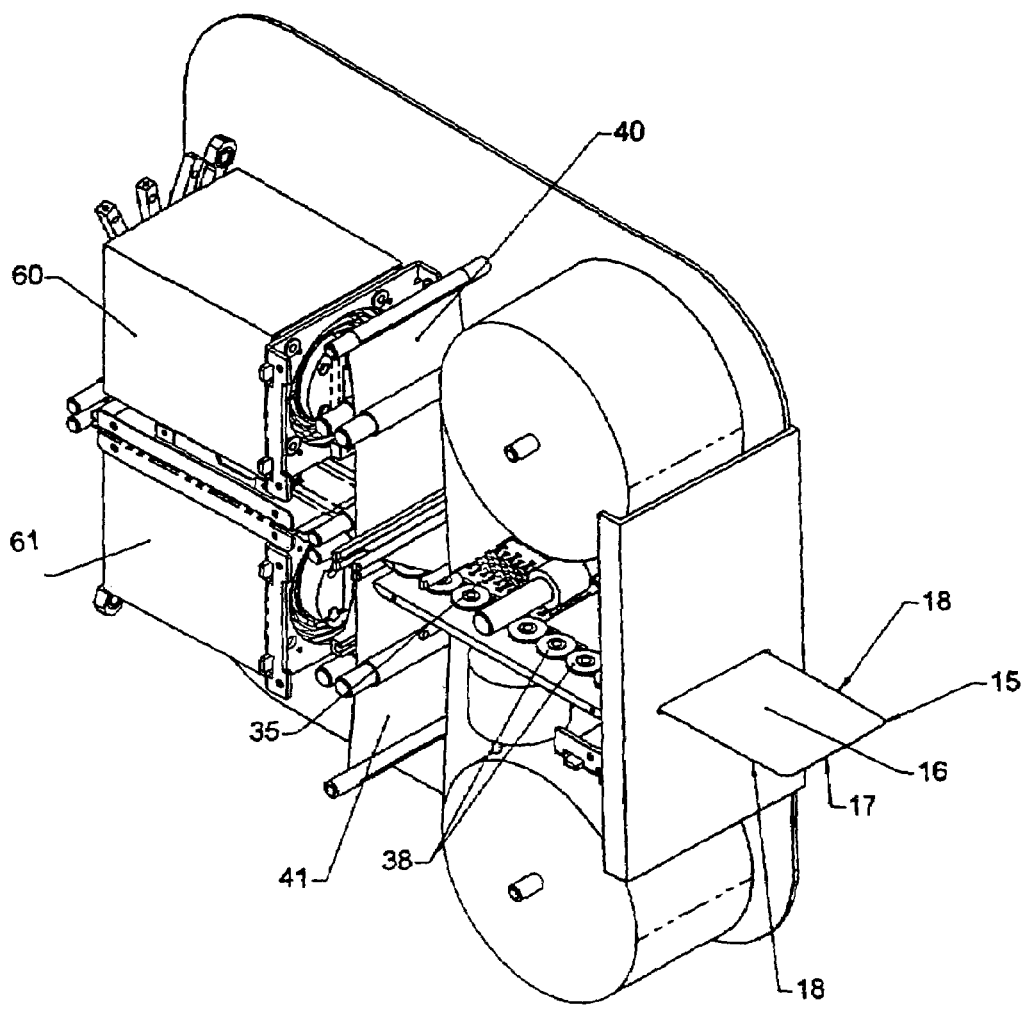
FIG. 9 is a perspective view of a contact trace detector according to another embodiment of the invention.

According to another embodiment, as shown in FIGS. 4, 8, and 9, the article processing mechanism 30, includes a guide roller 36 positioned on a bed 34. The article 15 is moved in one direction. The article 15, after being inserted through the entrance 22, is positioned between the bed 34 and the guide roller 36. Flat wheels 38 on the bed 34 move the article 15 along the bed 34. The article 15 is also assisted, as by pushing, by the guide roller 36. As the flat wheels 38 rotate along their axis, the flat wheels 38 frictionally contact the edges 18 of the article 15, moving the article 15 in the forward direction. In an embodiment, the guide roller 36 and/or flat wheels 34 can apply a substantially constant tension against the article 15. The guide roller 36 moves along a track 35 of the bed 34, keeping the article 15 in the correct path. The guide roller 36 and flat wheels 38 can be moved, for example, by a belt assembly.

Figure 1:
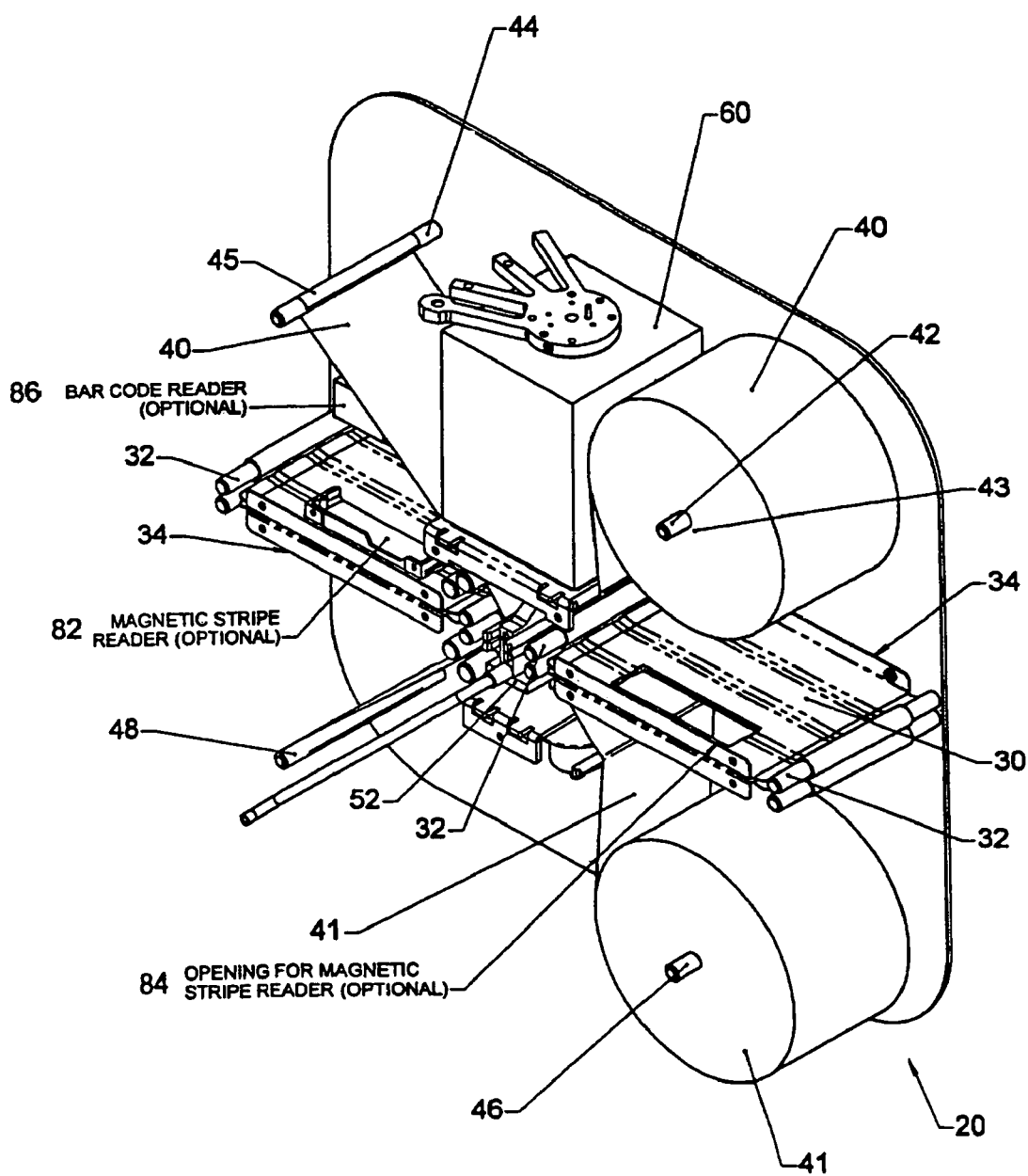
FIG. 1 is a perspective view of a detector according to a first embodiment of the invention.
Figure 2:
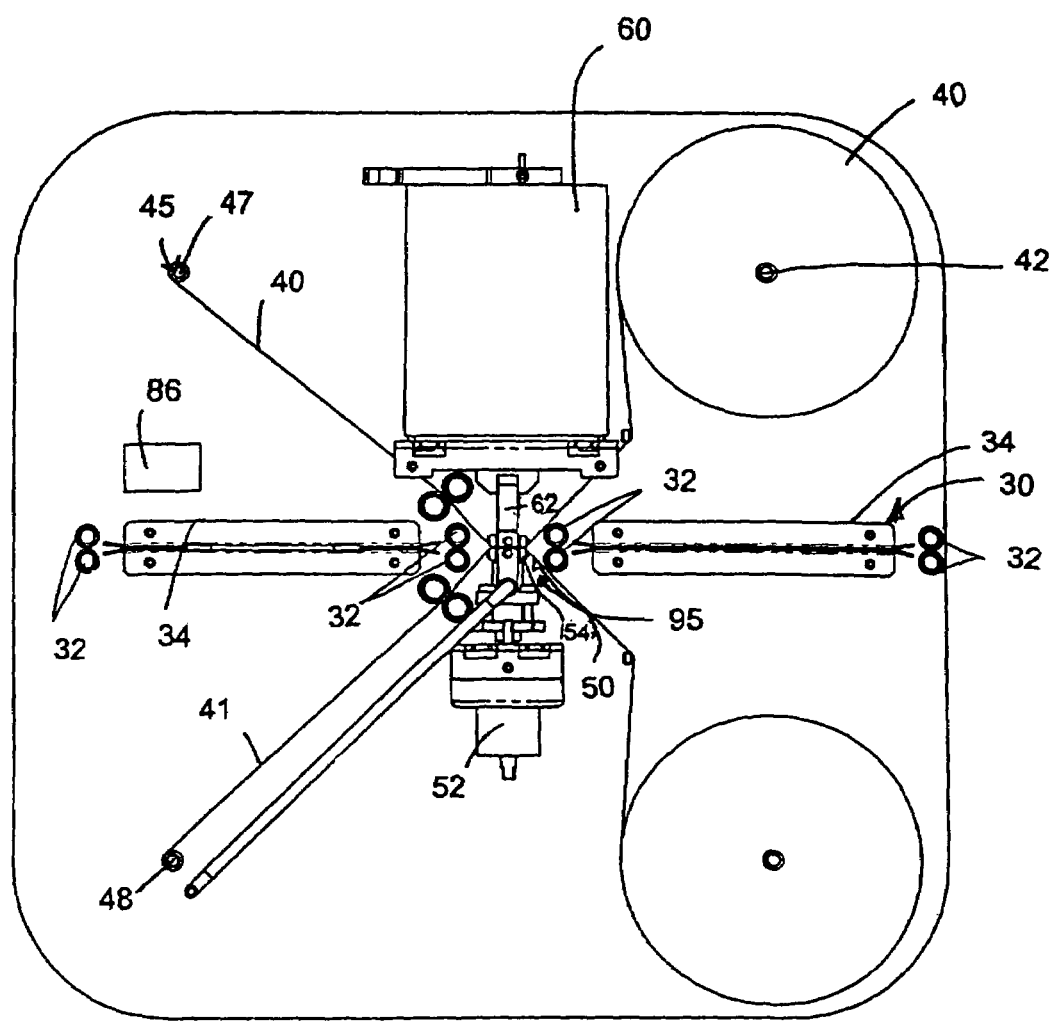
FIG. 2 is a front view of the contact trace detector according to FIG. 1.
Figure 3:
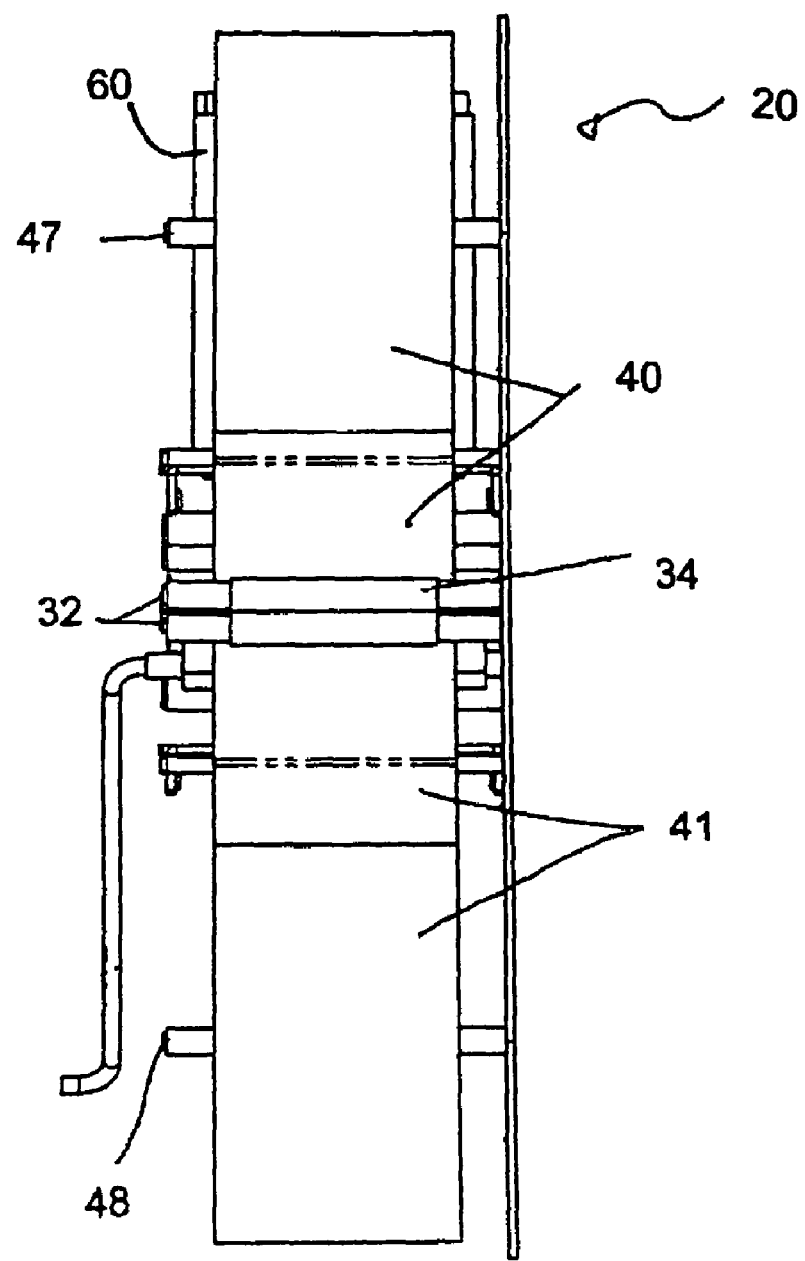
FIG. 3 is a side view of the contact trace detector according to FIG. 1.

According to another embodiment, the CTD 20 can include a magnetic reader 82, seen in FIG. 1. The magnetic reader 82 can be positioned after the switch mechanism 91, such that after an alarm is triggered and the article 15 is diverted to the holding area, the article 15 passes by the magnetic reader 82. The magnetic reader 82 reads the article 15 and transmits identifying information from the article 15 to the display panel 72. In another embodiment, a magnetic reader 82 can be positioned between the entrance and the swabbing area 95. It will be recognized that a combination of magnetic readers 82 may be used. In another embodiment, the CTD 20, as shown in FIG. 1, can include a mounting opening 84 for a magnetic reader 82. In a further embodiment, the CTD 20 can include a bar code reader 86. The bar code reader 86 can be positioned after the switch mechanism 91.

A swabbing medium 40 is used to collect a sample. The swabbing medium 40 can be any suitable material. As used herein, "swabbing medium 40," "swab" and "transfer substrate" are used interchangeably. "Swabbing medium 40," "swab" and "transfer substrate" refers to a substrate, such as a fabric, woven or non-woven, of any size suitable for the intended application.

The swabbing medium 40 should have absorption and desorption properties suitable for the analytes and substrates to be sampled, should be compatible with the geometry and processes performed by the instrument, should be durable and stable over a range of temperatures, and should be substantially free from contaminants and impurities capable in interfering with sample analysis.

The swabbing medium 40, according to another embodiment, should have the ability to absorb and/or adsorb an analyte upon contact with the swabbing medium 40, as well as efficiently desorb the analyte from the swabbing medium 40 upon placement of the swabbing medium 40 in the spectrometer 60. For example, the swabbing medium 40 should be able to effectively absorb/adsorb volatile substances into its fibrous structure or embed sample particles into its porous structure upon contact with an analyte present on the test surface. Additionally, the swabbing medium 40 should not interfere with a desorption process of a sample analyte from its surface or fibers during desorption of the collected sample.

According to another embodiment, a suitable swabbing medium 40 also should be durable and stable, capable of resisting decomposition and degradation due to heating and mechanical stress. Decomposition and degradation of the swabbing medium 40 can lead to contamination of the CTD 20, thus compromising the integrity of the analysis and potentially fouling the CTD 20. Decomposed and degraded fibers can generate false positives or can interfere with analyte detection resulting in failure in detecting an analyte. In addition, decomposed and degraded fibers can remain in the detection instrument, thus compromising subsequent analyses and risking damage to the detection instrument. The resistance of a swabbing medium 40 to decomposition and degradation is affected by physical properties of materials used, such as fiber strength, fiber length, fiber diameter, and smoothness of swabbing medium 40 fabric.

In one embodiment, the fabric or fiber is cellulosic. "Cellulosic" refers to any cellulose-derived fibers and fabrics, including, but not limited to cotton, linen, rayon, flax or blends thereof. According to another embodiment, the swabbing medium 40 can be, for example, Teflon®, Nomex®, Kevlar®, or a combination of Nomex® and Kevlar®. According to a further embodiment, the swabbing medium 40 comprises a stainless steel woven mesh for sample transfer.

The shape of the swabbing medium 40 can be, without limitation, circular, oval, square, rectangular, or any other shape suitable to purpose of the swabbing medium 40.

The swabbing medium 40 is contacted with an article 15 to be tested. The contacting step allows transfer of an analyte from the article 15 onto the swabbing medium 40. The swabbing medium 40 can be put into frictional contact with the article 15. The swabbing medium 40 can optionally gently squeeze the article 15, allowing one or more surface(s) 16, 17 of the article 15 to be rubbed by the swabbing medium 40. In an embodiment, the swabbing medium 40 can apply a substantially constant tension against the article 15, while in contact with the article 15.

The swabbing medium 40 can be supplied as a continuous strip or web. The swabbing medium can be conveyed by any combination of a least one roller as known in the art of converting machinery. The one or more rollers can be any suitable combination of driven and idle rollers capable of moving the swabbing medium adjacent to an article or article to be sampled. For example, the swabbing medium 40 can be fed substantially continuously from a feed coil 42, as shown in FIG. 1, while contacting the article 15.

The swabbing medium 40 can be regenerated and used more than one time or the swabbing medium 40 can be used a single time. The swabbing medium 40 can be regenerated continuously or in a batch mode. In one embodiment, the swabbing medium 40 can be have a first end 43 attached to a feed coil 42. A second end 45 can be attached to a second feed coil 44. The swabbing medium 40 can be positioned to unwind from the first feed coil 42, move adjacent to the article to be tested and adjacent to the spectrometer 60. The swabbing medium can then wind onto the second feed coil 44. The swabbing medium 40 can wind and/or unwind in either direction. The swabbing medium 40 is configured to contact the article 15 at a point between the first and second feed coil 42, 44, at the swabbing area 95.

According to another embodiment, the CTD 20 can comprise an additional or second swabbing medium 41. The second swabbing medium 41 is positioned on a feed coils 46, 48. The second swabbing medium can be configured similarly or differently from the first swabbing medium. The second swabbing medium 41 is positioned to contact a second surface 17 of an article 15, whereas the first swabbing medium 40 is capable of contacting a first surface 16 of an article 15. The first and second swabbing medium 40, 41 can be directed to the same spectrometer 60 within the detection system, in order to transfer a target analyte to the spectrometer 60. In another embodiment, the first swabbing medium 40 can be directed to a first spectrometer 60 and the second swabbing medium 41 can be directed to a second spectrometer 61, each within the same detection system. Each swabbing medium 40, 41 can contact a different surface 16, 17 of the article 15.

Figure 7:
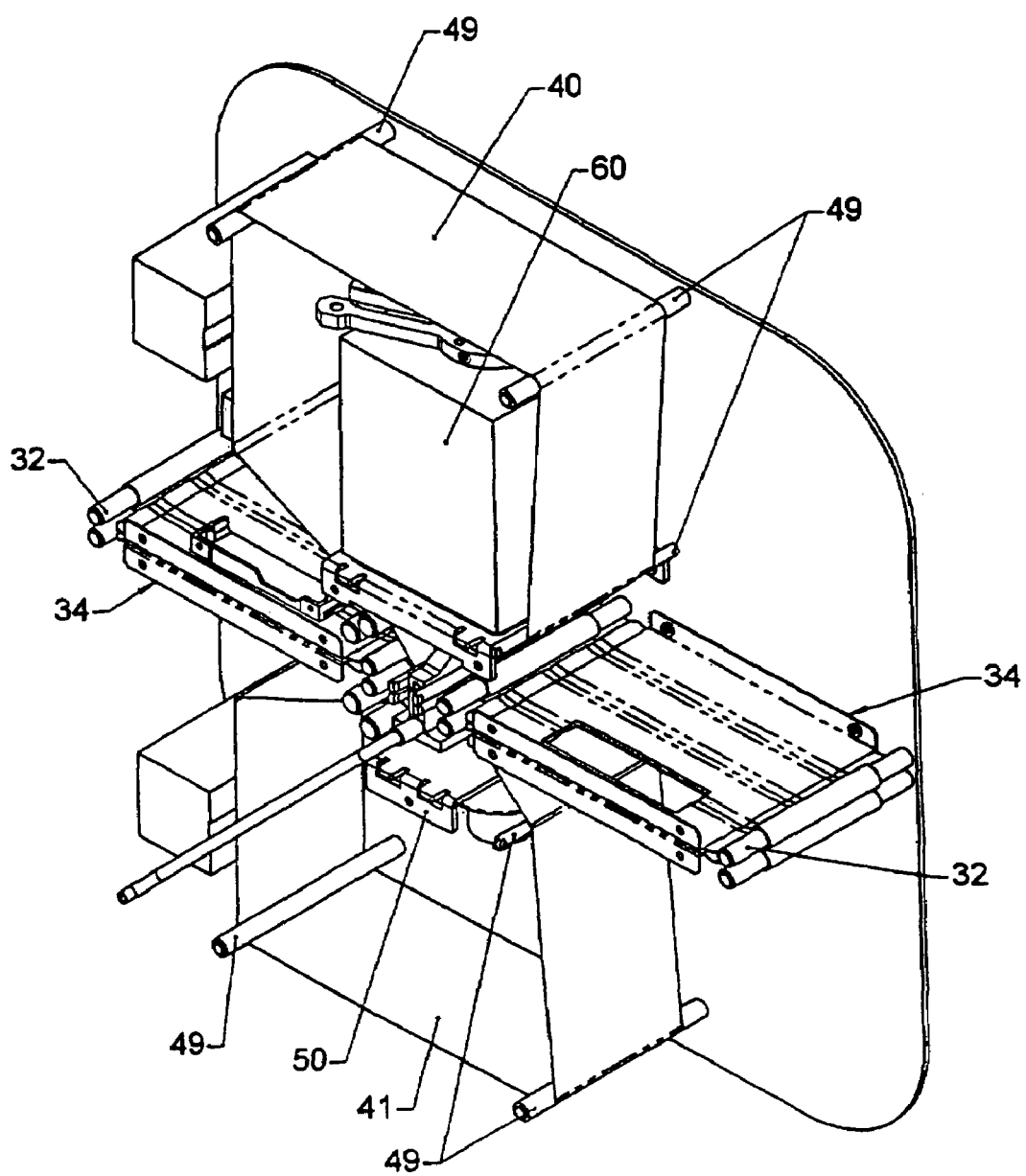
FIG. 7 is a perspective view of a contact trace detector according to another embodiment of the invention.

According to another embodiment, as shown in FIG. 7, the swabbing medium can be positioned around one or more swab posts 49. The CTD 20 can comprise multiple swab posts 49. The swabbing medium 40 wraps around the one or more swab post 49 and is capable of rolling over or around the posts. The one or more swabbing posts 49 can be fixed or rotating depending on the type of swabbing medium 40 used. In one embodiment, the swabbing medium 40 moves by synchronized motors, which rotate the posts and move the swabbing medium 40 in a forward and reverse direction as shown in, for example, FIG. 1. In another embodiment, the swabbing medium 40 moves by a belt assembly. The swabbing medium 40 comprises one continuous loop or web that rotates, as can be seen in FIG. 7.

The thermal desorber 50 desorbs a sample containing analytes from the swabbing medium 40. The thermal desorber can comprise any suitable means for heating the swabbing medium 40 such as, for example, electric resistance, an infrared source, or induction heating. In one embodiment, the thermal desorber 50 comprises a heater 54 and an anvil 52. The swabbing medium 40 containing a sample is positioned adjacent to the anvil 52. The anvil 52 is positioned adjacent to an inlet area 62 of a spectrometer 60. The anvil 52 is capable of moving relative to the spectrometer inlet. The anvil 52 can be moved using any suitable mechanism, such as, for example, an electromechanical drive. The anvil 52 can be moved towards an inlet area 62 of the spectrometer 60. A heater 54, which can be positioned within the anvil 52, is then activated, to desorb a sample on the swabbing medium 40. A portion or all of a desorbed sample can be carried by a carrier gas, such as, for example, air, through the anvil 52, the inlet area 62, and into the spectrometer 60 for analysis.

The anvil 52 can be any suitable size. In one embodiment, the dimension of the swabbing medium 40 and the inlet area 62 correspond with the dimensions of the spectrometer 60 such that either directly or indirectly (through the swabbing medium) the anvil 52 contacts the inlet area 62 when the anvil 52 is moved towards the inlet area 62 of the spectrometer 60.

The CTD 20 comprises a detection system, which detects the presence of a target analyte or compound. The detection system includes a spectrometer 60, and hardware and software for using the spectrometer 60. The hardware can comprise, for example, a CPU and corresponding electrical connections. The software includes a library of data for target analytes and compounds. When the spectrometer tests a target analyte, the spectrometer can compare the findings with the data in the library and determine the identity of the target analyte.

The CTD 20 and detection system can contain one or more spectrometers 60. The spectrometer 60 can employ ion mobility spectrometry, gas chromatography or a combination of these methods. In one embodiment, the spectrometer 60 is an ion mobility spectrometer (IMS) detector. IMS detectors are well known in the art, and are described, for example, in U.S. Pat. Nos. 5,405,781 and 5,071,771. In another embodiment, the spectrometer 60 can be the IONSCAN® 400B (Smiths Detection Inc.).

Figure 6:
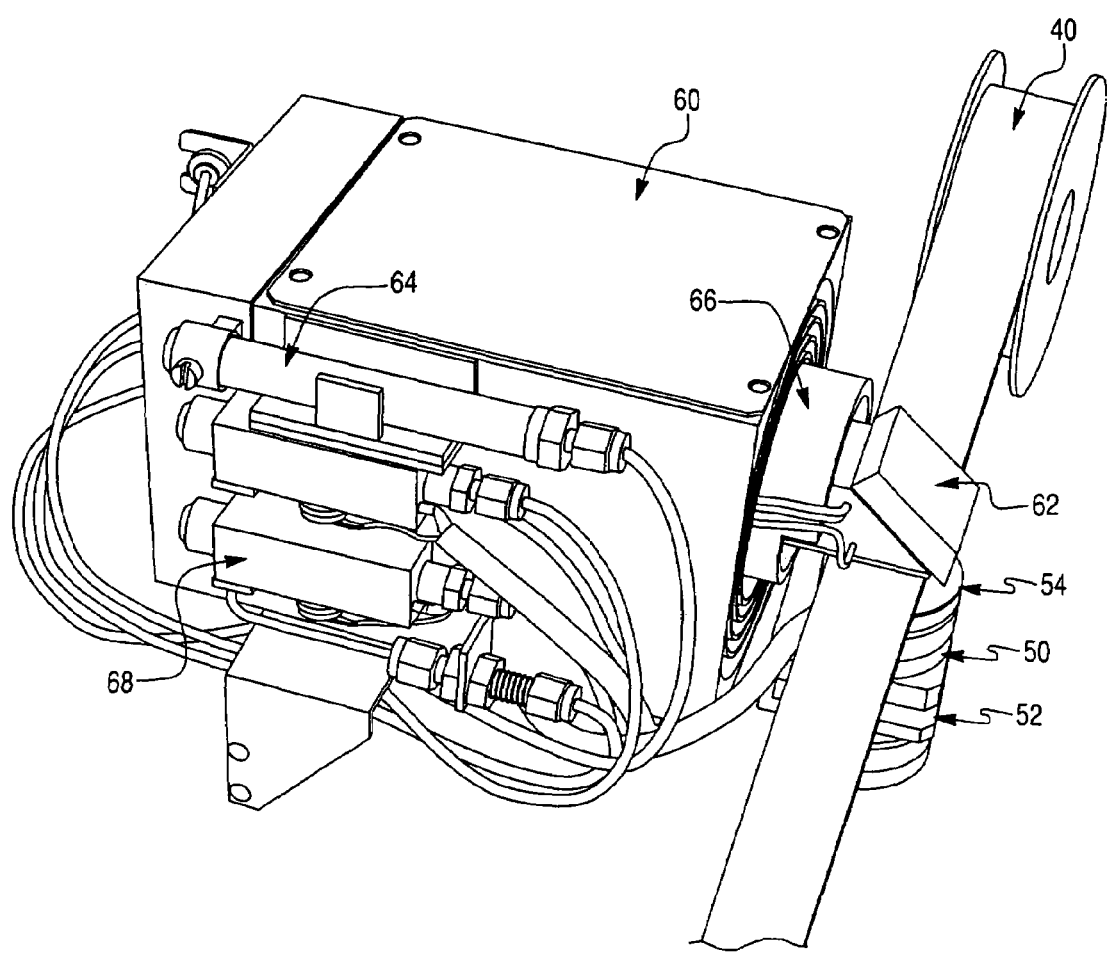
FIG. 6 is a perspective view of an ion mobility spectrometer.

The spectrometer 60, as seen in FIG. 6, comprises an inlet area 62, a condenser tube 64, a drift tube assembly 66, and a collector electrode or detector (not shown). The sample containing analytes enters the spectrometer 60 through the inlet area 62 after being heated by the thermal desorber 50. The condenser tube traps any sample effluents, preventing atmospheric discharge.

The spectrometer 60 optionally includes a calibrant block 68. The calibrant block 68 is used to check the overall performance of the system. The spectrometer 60 monitors calibrant recovery and suspends analysis until an acceptable level is reached.

The swabbing medium 40 is placed adjacent the inlet area 62 of the spectrometer 60. Analytes are liberated from the swabbing medium 40 by application of the desorber 50 heater 54. The inlet area 62 and desorber 50 can be operated at a temperature of approximately 200 to approximately 300° C. According to another embodiment, the inlet area 62 and desorber 50 temperatures can be operated at a temperature of approximately 220 and 225° C.

Desorbed analyte is carried into a reaction region by a carrier gas flow (not shown). Analyte is ionized in an ionization region using any suitable ionizing means. Suitable ionizing means include radioactive sources, such as $^{63}$Ni and 241 Am, and other sources Corona discharge and ultraviolet lamp. Ionized analyte is prevented from entering the drift region by the potential of a charged gating grid. When the gating charge is changed to a lower potential, the ions enter the drift region in the drift tube assembly 66; with the higher gating charge or potential present, the ions are prevented from entering the drift region. Within the drift region, ions are accelerated, under the influence of a strong electric field applied using focusing ring, through the drift region against a flow of drift gas towards a collector electrode.

According to an embodiment, the drift tube assembly can be operated at a temperature of approximately 55 to approximately 120° C. According to another embodiment, the drift tube assembly can be operated at a temperature of approximately 95° C. to approximately 115° C. According to another embodiment, the drift tube assembly can be operated at a temperature of approximately 110° C. The time required for a sample ion to reach the collector electrode is the "drift time." The drift time is a function of an ion's mobility and is a characteristic for an ion species. These species can then be classified according to their ability to be ionized, and to the relative mobilities of the ions produced. The resulting spectrum is analyzed to determine the presence of a target compound, namely an explosive material, chemical warfare compound, or narcotic, and a result is provided by the CTD 20.

According to an embodiment, the resulting identification of a target compound is reported on a display 72 of a control panel 70, shown in FIG. 4. According to another embodiment, the CTD 20 may also have a visual and/or audio alarm. The visual alarm may be shown on the display 72.

The CDT 20 can optionally include a second spectrometer 61. The second spectrometer 61 can operate independently from the first spectrometer 60. A sample for the second spectrometer 61 can be provided by a separate thermal desorption device or both the first 60 and the second 61 spectrometers can share a single thermal desorption device connected by, for example, a "Y" or "T"-shaped inlet. The inlet 62 can direct a thermally desorbed sample into each of two independent spectrometers 60, 61. Each spectrometer 60, 61 can receive a portion of a vaporized sample. In one embodiment, both the first 60 and second 61 spectrometers are IMS devices. The polarity, electric field gradient, temperature, gas flow, reactant and calibrant parameters for each of the first 60 and second 61 IMS can be independently controlled. Each of the first 60 and second 61 IMS has a means for providing an external reagent source. Each of the first 60 and second 61 IMS can have the same or different ionization sources.

The CTD 20, according to another embodiment, can include an air purification module 80. The air purification module 80 cleans the air within the CTD 20. Ambient air is used to provide supply gas for use as the drift and sample carrier gases for the IMS device operation. Other gas sources, e.g. compressed air, a commercial zero air purification system or another gas, can be used.

According to another embodiment, the CTD 20 can include a pump 90 for use with the spectrometer 60. Any suitable pump, such as, a rotary vane pump, RVP roughing pump, turbomolecular pumps, maglev turbomolecular pumps, high vacuum pumps, process integrated dry pumps, compact dry roughing pumps, and root pumps can be used. In one embodiment, the pump 90 is a vacuum pump. In another embodiment, the pump 90 is a diaphragm or piston pump or any other suitable pump.

According to another embodiment, the CTD 20 can include a controller (not shown). The controller controls all functions of the CTD 20, including movement of the article 15 within the CTD 20, spectrometer parameters, analysis of the spectrum obtained by the spectrometer 60, and output of the analysis and of spectrum. Any suitable control device can be used. In one embodiment, the controller comprises a CPU as provided in the Smiths IONSCAN® 400B (Smiths Detection Inc.). The controller may be housed in a card cage 88.

According to an embodiment, the CPU has at least three relay drivers available that can trigger features such as, for example, an alarm indication, including a visual and/or audible, and system status such as, for example, standby, ready and running.

The CTD 20 can optionally contain a front panel 70, keyboard, and a serial interface for communicating with a laptop for data collection and troubleshooting. According to another embodiment, the CTD 20 is capable of a network interface to provide the ability to monitor multiple CTDs 20, and, if desired data obtained from the multiple CTDs 20 can be reported to a central computer.

According to an embodiment, the CTD 20 can be interfaced with an entry/exit gate or door to control ingress and egress from an area based on the results obtained from the scanning of an article.

A method for detecting the presence of a target analyte using a CTD 20 is also provided. The article 15 can be inserted into the entrance 22 of the CTD 20. The article 15 is then guided by the rollers 32, 36, 38 and bed 34 of the article processing mechanism 30 through the CTD 20. The article 15 is guided to pass adjacent the swabbing medium 40 and frictionally contact the swabbing medium 40. The swabbing medium 40 contacts against a first surface 16 or a second surface 17 or both the first and second surfaces 16 and 17 of the article 15. The article processing mechanism 30 moves the article in a forward and reverse direction, allowing the surfaces 16, 17 of the article 15 to be contacted and, thus, transferring a sample to the swabbing medium 40. The article processing mechanism 30 can move the article 15 forward. The article 15 is then moved along a first path to the exit 24 or along a second path to a holding area 26. The swabbing medium 40 is positioned adjacent to a thermal desorption device and analyzed by a spectrometer. If, upon analysis, no target compound is detected, no alarm will be indicated and the article 15 travels along the first path to the exit 24. If a target analyte is detected, an alarm is indicated, and the article 15 travels along the second path to a holding area 26.

According to one embodiment, after a sample is obtained from the article 15 and disposed onto a swabbing medium 40, the anvil 52 contacts the swabbing medium 40. The heater 54 heats the swabbing medium 40, thermally desorbing the sample. The desorbed sample can be transferred by purge gas steam into the inlet area 62. The trace sample is then analyzed by the spectrometer 60. When a target analyte, such as an explosive material, chemical warfare agent, or narcotic is detected, the CTD 20 immediately triggers an "Alarm."

According to an embodiment of the invention, the purge gas steam can be approximately 100 cc/min to approximately 300 cc/min. According to another embodiment, the purge gas steam can be approximately 150 to approximately 250 cc/min. According to a further embodiment, the purge gas steam can be approximately 200 cc/min.

Effective sample collection is achieved when minimum force applied to the article 15, using friction and rubbing, exceeds the adhesion forces bonding the particles to the surface. For example, the force used to collect a sample is in the range of between approximately 0.0020 to 0.035 dynes. According to another embodiment, a range of approximately 0.0023 to 0.028 dynes. In a further another embodiment the force used to collect a sample is between 0.008 dynes to 0.020 dynes. In yet another embodiment, the force can be approximately 0.010 dynes to 0.018 dynes. According to a further embodiment, the force is approximately 0.012 dynes.

According to another embodiment, the method of detecting a target compound can include the use of a second swabbing medium 41. In this embodiment, the article 15 is moved in between the swabbing media 40, 41 and the first surface 16 of the article 15 is frictionally contacted against the swabbing medium 40, while the second surface 17 is frictionally contacted against the second swabbing medium 41. The swabbing media 40, 41 can apply substantially constant tension to the article 15 to prevent buckling or disorientation of the article 15.

According to another embodiment, the article processing mechanism 30 pushes and/or pulls the article 15 through the CTD 20 in one direction. The swabbing media 40, 41 are in frictional contact with the article 15 as it is fed through the CTD 20. The sample collected by the swabbing media 40, 41 can be directly vaporized into the spectrometer 60. After collecting a sample on the swabbing media 40, 41 and desorbing the sample from the swabbing media 40, 41, the swabbing media 40, 41 can be retained on the feed coils 42, 44, 46, 48.

According to a further embodiment, the CTD 20 includes a second spectrometer 61. In this embodiment, a first spectrometer 60 analyzes a sample collected on a first swabbing medium 40 and a second spectrometer 61 analyzes a sample collected on a second swabbing medium 41. As the article 15 is processed through the CTD 20, the first surface 16 of the article 15 contacts the first swabbing medium 40 and collects a trace sample. The second surface 17 contacts the second swabbing medium 41, collecting a first and a second sample. The first swabbing medium 40 is heated to desorb the sample for analysis in the first spectrometer 60 and the second swabbing medium 41 is heated to desorb a sample for analysis in the second spectrometer 61.

The process optionally can be automated to include a monitor of an internal calibrant to indicate that the system is ready. When the calibrant recover reaches an acceptable level a display 72 changes to display a "Ready" message on the screen. The spectrometer 60 can be programmed to execute a short cleaning cycle if calibrant recovery doesn't occur within approximately 10-12 minutes.

In a further embodiment, the method of detecting target analytes using the CTD 20 can be repeated. Furthermore, according to another embodiment, the CTD 20 may be controlled by a controller. The controller can be controlled by a computer. The controller may be programmed to have a cleaning protocol, which can include a baking protocol to clean the spectrometer or other CTD 20 components.

According to another embodiment, cleaning can be accomplished using a blank card soaked in a suitable solvent could also be used to clean the CTD 20 providing intimate contact with the whole processing mechanism.

According to a further embodiment of the invention, tokens can be used to verify or test the CTD 20. The tokens are spiked with traces of target analyte materials to verify overall system performance of the spectrometer 60. According to another embodiment, encapsulated explosive traces can be deposited on a dummy ticket 15 and boarding passes surfaces, which would be released by the roller action, and can provide a check on complete system performance.

Alternatively, according to another embodiment, a marker pen or lipstick containing small amounts of explosive materials can applied to a blank article 15 and run through the process.

The following examples are given for illustration. It should be understood, however, that the invention not be limited to the specific embodiments described in these examples. It will be apparent to those skilled in the art that various modifications and variations can be made to the embodiments without departing from the spirit or scope of the invention. Thus, it is intended that the present invention covers other modifications and variations of this invention within the scope of the appended claims and their equivalents.

EXAMPLE 1

Some commercial and natural products commonly found on an individual can potentially interfere with detection of target analytes by the CTD 20. These products are tested by applying the products to fingers and handling the documents 15. The documents are then swabbed with the medium and analyzed with the spectrometer 60.

Table 1 shows data obtained from the thermal desorption of known amounts of explosive materials deposited on clean swabbing medium 40. Sensitivities are determined based on the lowest amount deposited on the substrate which equaled or exceeded the Alarm threshold level for each explosive at a desorber 50 temperature of approximately 225° C.

TABLE 1

Signals from Thermal Desorption

| Explosive | Amount (pg) | Medium | Max Amp (du) | R F3 (du/mg) | LOD (ng) |
|---|---|---|---|---|---|
| DNT | 4,000 | Nomex1 | 754 ± 11% | 189 | 0.30 |
| NG | 250 | ... | 162 ± 9% | 648 | 0.10 |
| TNT | 300 | ... | 548 ± 10% | 1,827 | 0.03 |
| RDX | 500 | ... | 596 ± 80% | 1,192 | 0.05 |
| PETN | 500 | ... | 286 ± 20% | 572 | 0.10 |
| DNT | 4,000 | Kevlar2 | 315 ± 26% | 79 | 0.70 |
| NG | 250 | ... | 147 ± 8% | 588 | 0.10 |
| TNT | 300 | ... | 186 ± 17% | 620 | 0.10 |
| RDX | 500 | ... | 439 ± 15% | 878 | 0.06 |
| PETN | 500 | ... | 198 ± 11% | 396 | 0.13 |

The characteristics of Nomex and Kevlar are as follows: Nomex type E89, density 1.5 oz/sq. yd; 2 Kevlar type Z11, density 1.8 oz/sq. yd. The response factor is in digital units, dus, per nanogram of explosive. From field studies at airports, the practical limit of detection ("LOD") of contaminated swabs is 10-100× greater (depending upon type) than the above indicated values.

Occasionally, passengers will wear gloves when handling traveling documents 15. The purpose of a passenger using gloves is to avoid contamination of the article 15, and "fool" the CTD 20. To determine if a passenger has worn gloves to escape detection of target compounds by the CTD, characteristic oils exuded by the skin and present in fingerprints is analyzed. Peaks caused by theses oils do not interfere with target compounds and the absence of such peaks indicated that gloves may have been worn to avoid detection.

An analytical study of fingerprint oils found the following approximate percentage of chemical composition: Free fatty acids: 15-30; Mono, di and tri-glycerides: 35-60; Wax ester: 12-16; Squalene: 10-12; and Other: 2-5. The free fatty acids were mostly (over 90%) a combination of the C14-C18 isomers—Myristic, Palmitic, Stearic, Oleic and Linoleic acids.

Detection of these compounds in the spectrometer 60 indicates that the article 15 has been handled, but not necessarily by the passenger. Also, although this is a method to identify these fingerprint oils, the method is not foolproof, and cannot be traced specifically to the passenger. However, absence of these oils could generate a different type of Alarm and signal a "red flag" to the operator that maybe further investigation is warranted.

The effect of various creams, lotions, perfumes and aftershaves on explosive signals is shown below in Table 2. Nanogram levels of explosive materials are added to the swabbing medium 40 after it swiping a surface contaminated with the various commonly available substances listed.

TABLE 2

% Suppression of Explosive materials by Common Commercial Contaminants

|  | TNT | RDX | PETN | NG | AN |
|---|---|---|---|---|---|
| Amount Analyzed (ng) | 10 | 2 | 10 | 10 | 5 |
| Blank ticket 15 | 13-54 | 0 | 0 | 0-9 | 26-47 |
| Hand Lotions: | | | | | |
| Vaseline | 65 | 0 | 0 | 40 | 45 |
| Shiseido | 74 | 0 | 0 | 38 | 89 |
| Rim Corp | 52 | 0 | 0 | 41 | 66 |
| Perfumes: | | | | | |
| Obsession | 0 | 0 | 0 | 70 | 0 |
| Drakkar Noir | 26 | 0 | 0 | 20 | 0 |
| Jil Sander | 28 | 0 | 0 | 16 | 0 |
| Aftershave: | | | | | |
| Polo | 65 | 8 | 18 | 23 | 59 |
| Drakkar Noir | 71 | 12 | 7 | 48 | 66 |
| Azzaro | 79 | 10 | 13 | 50 | 54 |

% suppression is defined as $$\left(1 - \frac{\text{signal in presence of fingerprint}}{\text{signal from clean document}}\right) \times 100$$

The above are the average values from at least eight samples. The suppression effects of cosmetic products on TNT, NG and AN are significant, but these compounds are still detected at the nanogram level in the presence of much larger amounts of contaminants. This is consistent with reasonable levels of explosive materials expected to be found in practical deployment.

What is claimed is:

1. An contact trace detector, comprising:
   an article processing mechanism for moving an article through the detector,
   a swabbing medium for collecting an analyte from the article,
   a thermal desorber for desorbing the analyte from the swabbing medium, and
   a spectrometer with an inlet for receiving the analyte.

2. The contact trace detector of claim 1, wherein the desorber includes an anvil positioned adjacent the swabbing medium on a side opposite the inlet and configured to press the swabbing medium against the inlet.

3. The contact trace detector of claim 2, further comprising:
   a heater movable with the anvil and configured to heat the analyte.

4. The contact trace detector of claim 1, wherein the swabbing medium comprises a fabric.

5. The contact trace detector of claim 1, wherein the swabbing medium comprises a steel woven mesh.

6. The contact trace detector of claim 1, wherein the article processing mechanism comprises a roller positioned adjacent a guide bed to move the article proximate the swabbing medium.

7. The contact trace detector of claim 6, wherein the roller applies a tension against the article.

8. The contact trace detector of claim 1, wherein the swabbing medium is attached to a feed roller to feed the swabbing medium against the article.

9. The contact trace detector of claim 1, further comprising:
an air purification module for cleaning the air within the detector; and
a controller, wherein the controller controls the movement of the article processing mechanism.

10. The contact trace detector of claim 1, wherein the swabbing medium applies a tension against the article.

11. The contact trace detector of claim 1, further comprising:
a guide bed, and
a plurality of rollers, comprising:
a first roller set with at least one roller; and
a second roller set with at least one roller,
wherein the first roller set is positioned opposite the second roller set and configured to move the article between the first roller set and the second roller set.

12. The contact trace detector of claim 11, wherein the first roller set and the second roller set are capable of rotating in a forward and backward direction.

13. The contact trace detector of claim 11, further comprising:
a switch mechanism, wherein the switch mechanism includes at least one roller to change a travel path of the article between a path to the exit area and a path to the holding area.

14. The contact trace detector of claim 13, wherein the switch mechanism is activated by a solenoid.

15. The contact trace detector of claim 1, wherein the article processing mechanism includes at least one guide roller and at least one flat wheel positioned on a bed, wherein the guide roller is positioned on a first side of the article and the bed is positioned on a second side of the article.

16. The contact trace detector of claim 1, further comprising a magnetic reader for reading information from the article.

17. The contact trace detector of claim 1, further comprising a second swabbing medium for collecting an analyte from the article, wherein the first swabbing medium contacts a first surface of the article and the second swabbing medium contacts a second surface of the article.

18. The contact trace detector of claim 1, wherein the swabbing medium contacts at least one roller.

19. The contact trace detector of claim 1, wherein the swabbing medium includes a first end attached to a first feed coil and a second end attached to a second feed coil.

20. The contact trace detector of claim 17, further comprising a second spectrometer with an inlet for receiving the analyte, wherein the second spectrometer analyzes analyte obtained from the second swabbing medium.

21. A method of testing an article, comprising:
inserting an article into a detector, the article having a first surface and a second surface;
contacting a first surface of the article with a first swabbing medium while the article is present in the detector;
transferring an analyte to the swabbing medium; and
analyzing the analyte.

22. The method of claim 21, further comprising contacting the second surface of the article with a second swabbing medium while the article is present in the detector.

23. The method of claim 22, further comprising desorbing the analyte from the first surface of the article from the swabbing medium into a first ion mobility spectrometer, and desorbing the analyte from the second surface of the article from the second swabbing medium into a second ion mobility spectrometer.

24. The method of claim 22, further comprising desorbing the analyte from the first surface of the article from the swabbing medium into an ion mobility spectrometer, and desorbing the analyte from the second surface of the article from the second swabbing medium into the ion mobility spectrometer.

25. The method of claim 21, further comprising:
moving the swabbing medium to a desorber region,
contacting the swabbing medium with an anvil, and
heating the swabbing medium.

26. The method of claim 21, further comprising:
transferring the analyte from the swabbing medium to a spectrometer, wherein the spectrometer analyzes the analyte.

27. The method of claim 26, wherein the spectrometer is an ion mobility spectrometer.

28. The method of claim 21, wherein tension is applied to the article when the article is in contact with the swabbing medium.

29. The method of claim 21, wherein the swabbing medium comprises a fabric.

30. The method of claim 29, wherein the fabric is supplied by a feed roller.

31. A method of testing an article, comprising:
(a) inserting an article into a detector, the article having a first surface and a second surface;
(b) contacting a first surface of the article with a first swabbing medium;
(b) transferring an analyte to the swabbing medium; and
(c) analyzing the analyte,
wherein the swabbing medium comprises a steel woven mesh.

32. The method of claim 21, further comprising positioning the article proximate the swabbing medium using at least one roller.

33. The method of claim 21, further comprising vaporizing the analyte to release the analyte from the swabbing medium, wherein the vaporized analyte is transferred to a spectrometer.

34. A method of testing an article, comprising:
(a) inserting an article into a detector, the article having a first surface and a second surface;
(b) contacting a first surface of the article with a first swabbing medium;
(c) transferring an analyte to the swabbing medium; and
(d) desorbing the analyte on the swabbing medium; and
(e) moving the swabbing medium on a feed wheel after desorption; and
(f) analyzing the analyte.

* * * * *